US012653713B2

(12) United States Patent (10) Patent No.: US 12,653,713 B2
Yazawa (45) Date of Patent: Jun. 16, 2026

(54) PORTABLE THERMAL THERAPY SYSTEM

(71) Applicant: Purdue Research Foundation, West Lafayette, IN (US)

(72) Inventor: Kazuaki Yazawa, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 854 days.

(21) Appl. No.: 17/011,980

(22) Filed: Sep. 3, 2020

(65) Prior Publication Data

US 2021/0059854 A1 Mar. 4, 2021

Related U.S. Application Data

(60) Provisional application No. 62/895,297, filed on Sep. 3, 2019.

(51) Int. Cl.
A61F 7/00 (2006.01)
A61F 7/02 (2006.01)

(52) U.S. Cl.
CPC ............... *A61F 7/007* (2013.01); *A61F 7/02* (2013.01); *A61F 2007/0054* (2013.01);
(Continued)

(58) Field of Classification Search
CPC ...... A61F 2007/0054; A61F 2007/0075; A61F 2007/0055–56; A61F 2007/0076; A61F 2007/0059; A61F 2007/0063; A61F 2007/0069; A61F 2007/0233–0238; A61F 2007/0228–023
See application file for complete search history.

(56) References Cited

U.S. PATENT DOCUMENTS 6,097,088 A * 8/2000 Sakuragi ................. C30B 29/46
257/467
7,959,657 B1 * 6/2011 Harsy ..................... A61F 7/007
607/104
(Continued)

FOREIGN PATENT DOCUMENTS

WO WO-2011156643 A1 * 12/2011 ............. A61F 7/007

OTHER PUBLICATIONS

Tellurex Corporation. Appendix E: The Most Frequently Asked Questions About Thermoelectric Cooling. pp. 2-3 (Year: 2006).*
(Continued)

*Primary Examiner* — Linda C Dvorak
*Assistant Examiner* — Davina E. Lee
(74) *Attorney, Agent, or Firm* — Maginot, Moore & Beck LLP

(57) ABSTRACT

A system for applying thermal therapy includes a portable housing and at least one conduit supportable in proximity to body tissue, the conduit having an inlet end and outlet end. The housing supports at least one thermoelectric module, a power storage unit, a pump, a fluid inlet and a fluid outlet. The fluid inlet and fluid outlet are to the inlet and outlet of the conduit. The pump is operably connected to pump fluid from the fluid inlet to the fluid outlet. The at least one thermoelectric module is coupled to generate a thermal change in fluid disposed between the fluid inlet and the fluid outlet. The power storage unit is operably coupled to provide operating power to the pump and the at least one thermoelectric module.

15 Claims, 4 Drawing Sheets

(52) U.S. Cl.
CPC ................. *A61F 2007/0075* (2013.01); *A61F 2007/0077* (2013.01); *A61F 2007/0233* (2013.01)

(56) References Cited

U.S. PATENT DOCUMENTS

| | | | |
|---|---|---|---|
| 8,894,698 B2 | 11/2014 | Gammons et al. | |
| 9,283,109 B2 * | 3/2016 | Guyuron ................... | A61F 7/02 |
| 10,350,108 B1 * | 7/2019 | Rittman, III .............. | A61F 7/02 |
| 2013/0331914 A1 * | 12/2013 | Lee .......................... | A61F 7/007 607/96 |
| 2014/0222121 A1 * | 8/2014 | Spence ..................... | A61F 7/02 607/104 |
| 2014/0352325 A1 * | 12/2014 | Brown ................... | A61B 18/02 62/3.2 |
| 2015/0216718 A1 * | 8/2015 | Diller ..................... | A61F 7/007 607/96 |
| 2015/0335468 A1 * | 11/2015 | Rose .................... | A61F 7/0085 607/104 |
| 2017/0071783 A1 * | 3/2017 | Calderon ................. | A61F 7/02 |
| 2018/0193186 A1 * | 7/2018 | Wright ................. | A61F 7/0085 |
| 2018/0360650 A1 * | 12/2018 | Asirvatham ....... | A61B 18/1402 |
| 2019/0099288 A1 * | 4/2019 | Vergara .................... | F28F 9/18 |
| 2019/0099290 A1 * | 4/2019 | Thomas ................... | A61F 7/08 |
| 2019/0350752 A1 * | 11/2019 | Aguiar ...................... | A61F 7/02 |
| 2020/0138665 A1 * | 5/2020 | Binversie ............... | A61F 7/007 |
| 2021/0060230 A1 * | 3/2021 | Hopper ............ | A61M 1/36222 |

OTHER PUBLICATIONS

Stryker, "T/Pump: Localized Therapy System," Information and Specifications Sheet, USA, 2017 (2 pages).

* cited by examiner

PORTABLE THERMAL THERAPY SYSTEM

This application claims the benefit of U.S. Provisional Patent Application Ser. No. 62/895,297, filed Sep. 3, 2019, which is incorporated herein by reference in its entirety.

FIELD OF THE INVENTION

The present invention relates to systems and methods for providing temperature-based therapy to portions of the anatomy.

BACKGROUND

In general, thermal therapy involves applying heating (i.e. thermotherapy) and/or cooling (i.e. cryotherapy) to parts of the anatomy of a living thing, such as a human being. For example, it is common to apply an ice pack or similar chilled pack to a body part after strain to reduce inflammation, and to sometimes apply heat to relax muscles. The benefits of both hot and cold thermal therapy are well known and varied.

Thermotherapy can be achieved by placing heated pads over the anatomical area to be treated. Pads may be heated by electrical current through resistive elements, stored heated water or other liquid, or by chemical reaction. One issue with heated pads is that they are difficult to make portable for many reasons. Many electricity based heating pads are powered by the AC mains, and therefore have a power cord. Heating pads that are in the form of hot water bottles are difficult to keep over the area to be treated if the person is ambulatory. Most heating pads of all types merely drape or lay on or under the body part, and cannot self-support during movement. Another drawback is that most heating pads cannot easily be wrapped to cover all sides of a limb, such as for treating knees, calves, ankles, forearms, shoulders and the like.

It is known to use wrapped heating elements, sleeves or boots, to help retain a heating element against a limb or body part during movement. However, a good solution allowing sustained heating and ambulatory movement has proven evasive.

Cryotherapy has similar problems. Cryotherapy often involves ice packs and/or ice baths. Neither is particularly conducive to movement, and requires the ready availability of ice or other chilled structure or liquid.

There is a need, therefore, for method and apparatus capable of providing localized thermotherapy and/or cryotherapy that allows for movement of the subject.

SUMMARY

At least some embodiments described herein address the above-stated need, as well as others by providing a portable and wearable system for applying cool or warm liquid to a body part.

A first embodiment is a system for applying thermal therapy that includes a portable housing and at least one conduit supportable in proximity to body tissue, the conduit having an inlet end and outlet end. The portable housing supports at least one thermoelectric module, a power storage unit, a pump, a fluid inlet and a fluid outlet. The fluid inlet is configured to be operably coupled to the outlet end of the at least one conduit, and a fluid outlet is configured to be operably coupled to the inlet end of the at least one conduit. The pump is operably connected to pump fluid from the fluid inlet to the fluid outlet. The at least one thermoelectric module is coupled to generate a thermal change in fluid disposed between the fluid inlet and the fluid outlet. The power storage unit is operably coupled to provide operating power to the pump and the at least one thermoelectric module.

The above-described features and advantages, as well as others, will become more readily apparent to those of ordinary skill in the art by reference to the following detailed description and accompanying drawings.

DETAILED DESCRIPTION

Figures 1, 2:
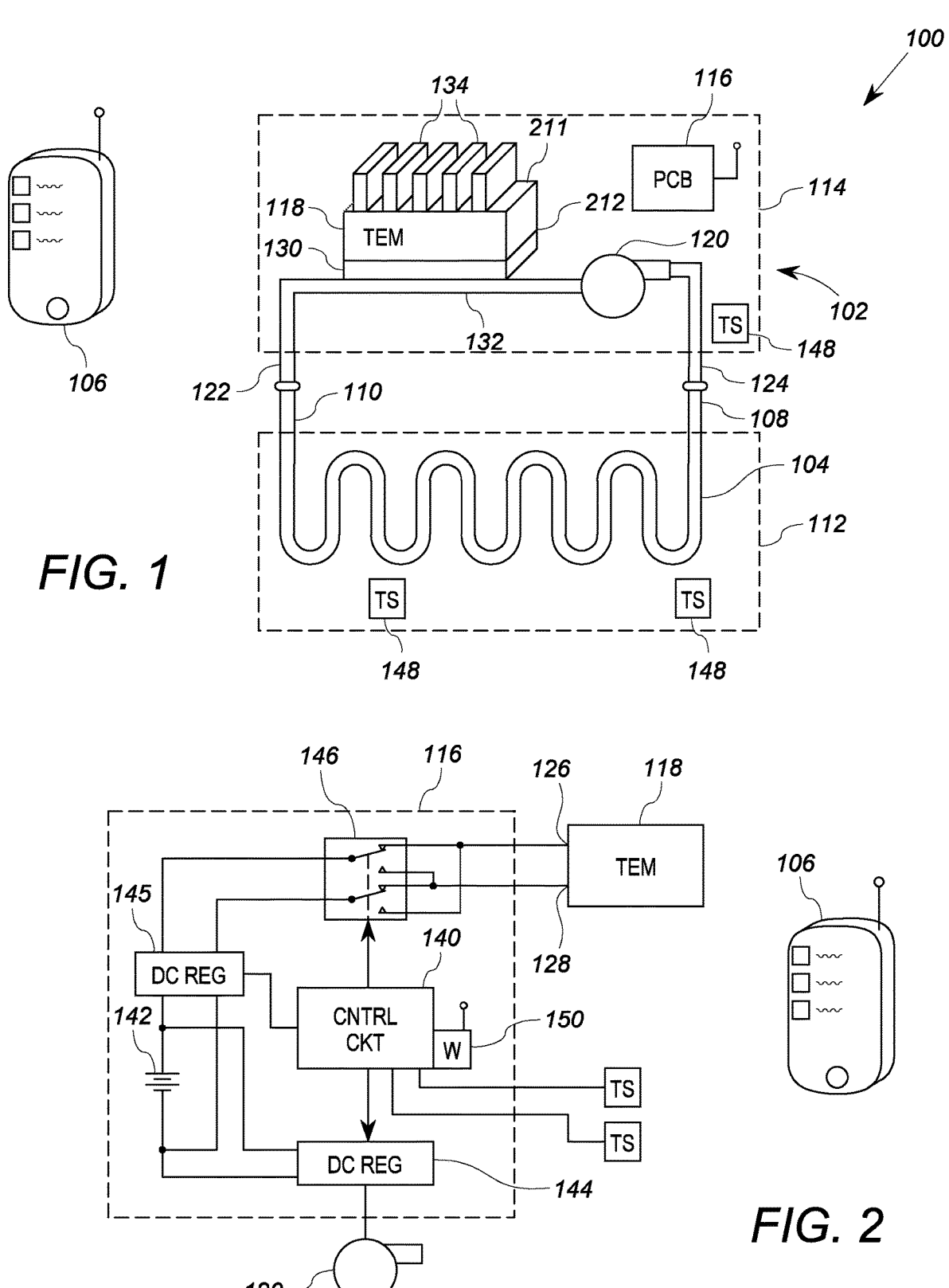
FIG. 1 shows a representation of mechanical elements of a portable thermal therapy system according to an exemplary first embodiment.
FIG. 2 shows a schematic representation of the electrical elements of the portable thermal therapy system of FIG. 1.

An exemplary embodiment of an improved thermal therapy system 100 is shown in FIGS. 1 and 2. FIG. 1 shows a representative diagram of mechanical features of a portable thermal therapy system 100, while FIG. 2 shows a schematic representation of the electrical elements of the system 100. The system 100 in this embodiment includes a self-powered, portable thermal pack 102, an application conduit 104, and wireless computing device 106, for example, a smart phone.

The application conduit 104 comprises at least one fluid conduit supportable in proximity to body tissue to exchange heat therewith. The conduit 104 is configured to convey fluid therethrough, and has an inlet end 108 and outlet end 110. In this embodiment, the inlet end 108 end includes a coupling 108a, and the outlet end likewise includes a coupling 110a. In some embodiments, the inlet end 108 and the outlet end 110 are interchangeable. The application conduit 104 is constructed to have good thermal conductance, suitably using materials known in the art for such purpose.

In general, the application conduit 104 is integrated into a garment 112 that may be affixed around, on or to a body part to which the thermal therapy is to be applied. The garment 112 is configured such that heat exchange occurs between the body part of interest and the fluid within the conduit 104. Suitable devices are known. For example, U.S. Pat. No. 8,894,698, which is incorporated herein by reference, shows a series of wrapping garments with affixed fluid conduits that may be applied to various body portions. Other examples could include sleeves, pants, shirts, knee braces, stockings, helmets, neck braces, etc., which have a conduit woven into or formed in the garment fabric or material, or otherwise secured such that conduit 104 can exchange heat with the body on which garment 112 is worn.

In some embodiments, one or more temperature sensors 148 may also be incorporated into or on the garment 112 to obtain temperature information regarding the area of the body being treated, the garment 112 and/or the conduit 104 itself. As will be discussed below, the temperature sensors 148 are configured and/or are operably coupled to convey temperature information to a device external to the garment 112.

The portable thermal pack 102 includes a portable housing 114 that supports and/or contains a printed circuit board 116, at least one thermoelectric module 118, at least one pump 120, and a supply conduit 132 for transferring fluid. The supply conduit 132 includes at one end a fluid inlet 122 configured to be operably coupled to the outlet end 110 of the at least one conduit 104, and at the other end a fluid outlet 124 configured to be operably coupled to the inlet end 108 of the at least one conduit 104. The portable housing 114 may have the general structure of a wearable pack or satchel.

Figure 3:
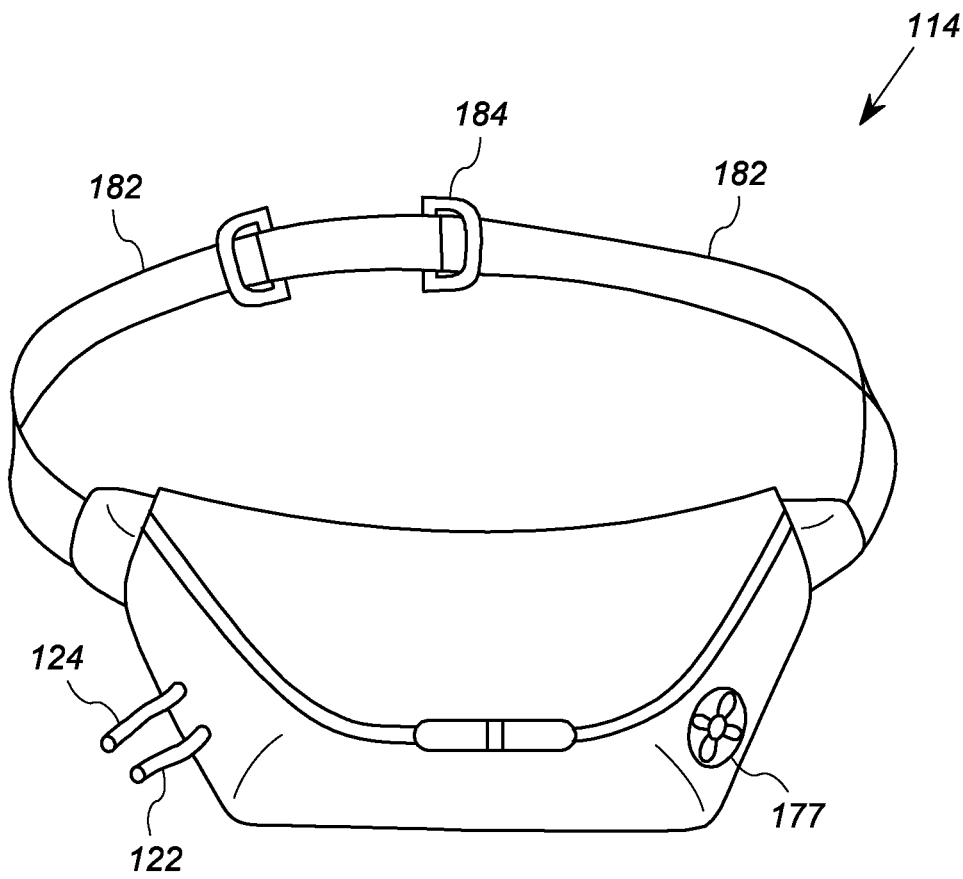
FIG. 3 shows a perspective view of an exemplary portable housing of the portable thermal therapy system of FIG. 1.

For example, FIG. 3 shows an exemplary embodiment of the portable housing 114 in the form of a waist pack or satchel 180 that is worn on the waist of a human, and has a belt 182 that extends around the abdomen and connects with a snapping buckle or clasp 184. In this embodiment, the satchel 180 includes a battery operated fan 177 configured to move air through the satchel 180 for improved thermal exchange with the ambient air 181. Referring again to FIG. 1, other portable housings 114 could be based on shoulder packs or other wearable satchels. It will be appreciated that the satchel 180 may readily house a fixture, not shown, such as a plastic frame or box, that contains or supports the printed circuit board 116, the at least one thermoelectric module 118, the pump(s) 120, and the supply conduit 132. The satchel 180 also can store the portable computing device 106. In the embodiment of FIG. 3, the fluid inlet 122 and fluid outlet 124 extend out of the satchel 180 to allow for easy connection and disconnection to the application conduit 104.

It will be appreciated that the portable housing 114 and garment 112 may be adopted for non-human animals, such as livestock or domestic pets. The effects of thermal therapy can be beneficial to animals for reasons that include, but are not limited to, the same reasons thermal therapy is beneficial to humans. It will be appreciated that the garment 112 and portable housing 114 may be separate structures, or combined in some circumstances, depending on what portion of the animal is intended to receive the therapy.

Referring again to FIG. 1, the pump 120 is operably connected to pump fluid from the fluid inlet 122 to the fluid outlet 124. The pump 120 is battery powered.

The thermoelectric module 118 is operably coupled to generate a thermal change in fluid that flows the supply conduit 132 between the fluid inlet 122 and the fluid outlet 124. To this end, the thermoelectric module 118 may be a suitable commercially available thermoelectric module such as those available from Ferrotec at ferrotec.com. In general, a suitable example of a thermoelectric module 118 is shown in perspective view in FIG. 4.

Figure 4:
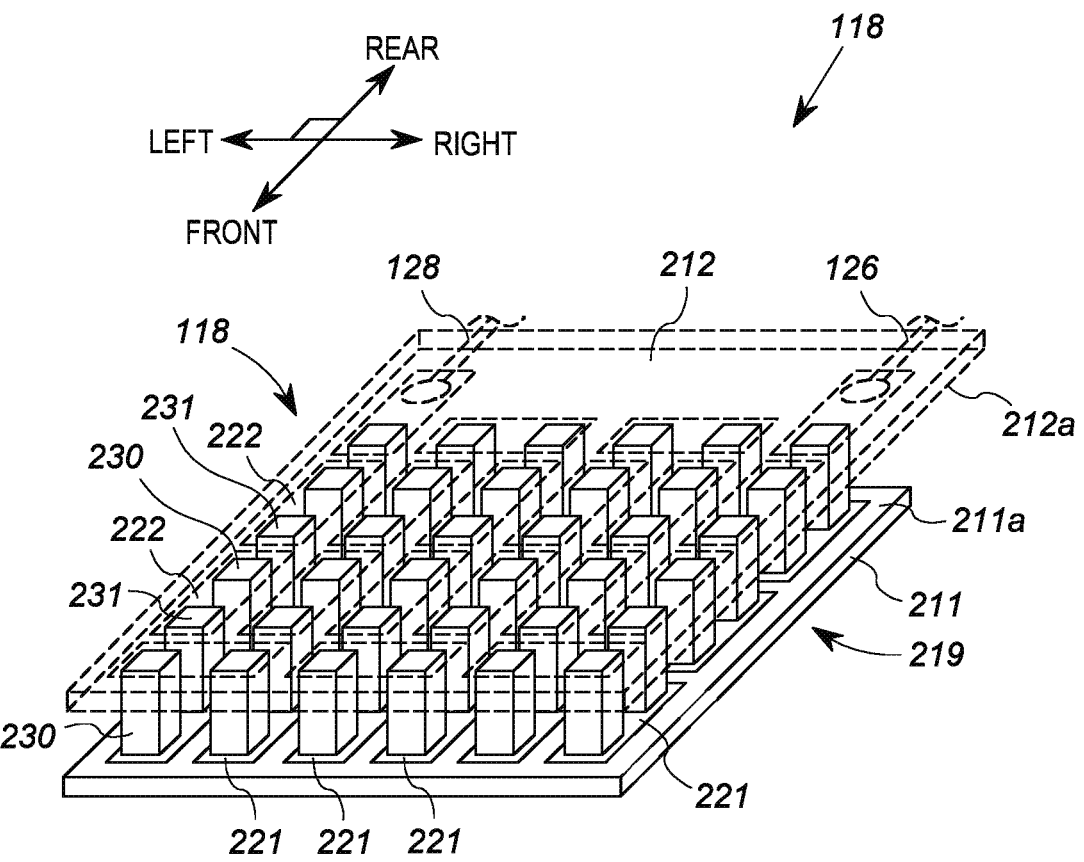
FIG. 4 shows a perspective view of an exemplary thermoelectric module that may be used in the portable thermal therapy system of FIG. 1F.

In the exemplary embodiment of FIG. 4, the thermoelectric module 118 includes two insulating substrates 211, 212, plural electrodes 221, 222, and a plurality of Peltier elements 230, 231. The electrodes 221, 222 are formed on the insulating substrates 211, 212 respectively. The plural Peltier elements 230, 231 are mounted to each of electrodes 221, 222. The insulating substrates 211, 212 have a substantially plate-like shape, and may suitably be made of aluminum or other material.

The electrodes and Peltier elements are mounted to a first surface 211a of the first insulating substrate 211 that faces the second insulating substrate 212. Similarly, the electrodes and Peltier elements are mounted to a first surface 212a of the second insulating substrate 212 facing the first insulating substrate 211. The electrodes 221 are formed on the first side 211a of the first insulating substrate 211, and the electrodes 222 are formed on the first side 212a of the second insulating substrate 212. The electrodes 221, 222 are formed in strip shapes and have substantially similar configurations.

Each of the first electrodes 221 includes a first side abutting the first insulating substrate 211 and an opposing second side. Two Peltier elements 230, 231 are mounted (soldered) onto the second side of each of the first electrode 221 in a longitudinal direction. The Peltier elements 230, 231 are mounted (soldered) onto the second electrode 222 in a similar manner. The Peltier elements 230 are formed as P-type Peltier elements and the Peltier elements 231 are formed as N-type Peltier elements. As illustrated in FIG. 1, each of the Peltier elements are connected so that the P-type Peltier elements 230 and the N-type Peltier elements 231 are arranged alternately in series via the electrodes 221 and the electrodes 222.

The thermoelectric module 118 further includes first and second terminals 126, 128. The plurality of Peltier elements 230, 231 are series connected (as described above) by alternating doping type between first and second electrical terminals 126, 128. The thermoelectric module 118 is actuated by applying a voltage across the first and second terminals 126 and 128. The operation of thermoelectric module 118 under excitation voltages is known in the art, and will vary based on the specific configuration of the thermoelectric module 118, which can vary from that shown in FIG. 4.

It will be appreciated that the thermoelectric module 118 may take other forms of thermo electric devices that develop a temperature gradient or different between one substrate (i.e. substrate 211) and another substrate (i.e. substrate 212) in response to current, based on thermoelectric properties of suitable semiconductors.

Referring again to FIG. 1, the second insulating substrate 212 is operably coupled to convey exchange heat with fluid within the housing 114 via a thermally conductive plate, bar, or wrap 130 that is in contact with and in a heat exchanging relationship with, the supply conduit 132. The first insulating substrate 211 is preferably affixed to heat sink fins 134. The heat sink fins 134 facilitate exchange of heat between the first insulating substrate 211 and the air.

Figure 5:
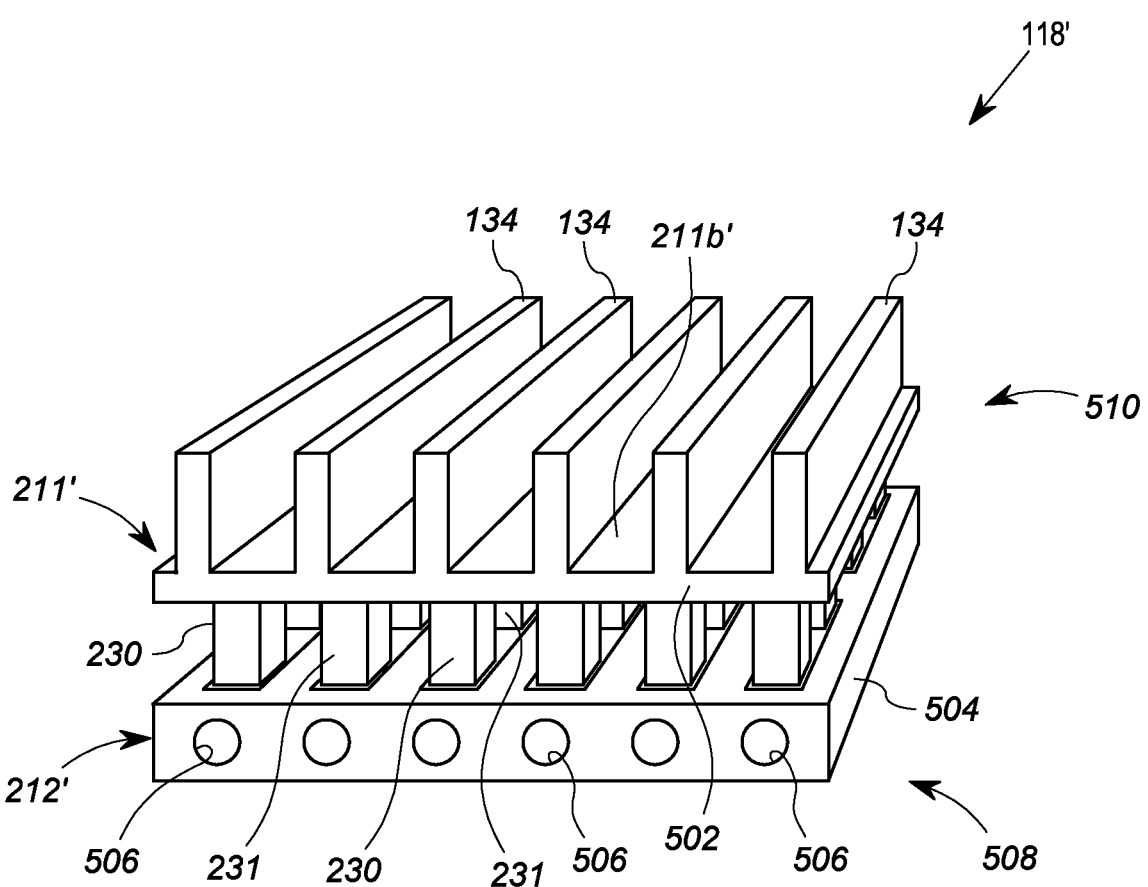
FIG. 5 shows a plan view of an alternative embodiment of a thermoelectric module that may be used in the portable thermal therapy system of FIG. 1.

It will be appreciated that in some embodiments, the thermoelectric module 118 (or other suitable thermoelectric modules) can be integrally formed or otherwise include the thermally conductive element 130 and/or the heat sink fins 134. In other embodiments, the thermally conductive element 130 and/or the heat sink fins 134 are separate elements. FIG. 5 shows a plan view of an alternative embodiment of a thermoelectric module 118' that may be used in the portable thermal pack 102 which includes both the thermally conductive element that exchanges heat with the fluid in the supply conduit 132 and heat sink fins. The thermoelectric module 118' may suitably have the same construction as the thermoelectric module 118 of FIG. 4, except that the first insulating substrate 211 and second insulating substrate 212 have been replaced by a different first insulating substrate 211' and second insulating substrate 212', respectively. Elements common to both the thermoelectric module 118 and the thermoelectric module have like reference numbers. However, it will be appreciated that the insulating substrates 211' and 212' may be used in connection with other embodiments of thermoelectric devices.

In the exemplary embodiment of FIG. 5, the thermoelectric module 118' includes the two insulating substrates 211', 212', plural electrodes, not shown but similar to electrodes 221, 222 of FIG. 3, and a plurality of Peltier elements 230, 231. Similar to the electrodes 221, 222 of FIG. 3, the electrodes are formed on the insulating substrates 211', 212' respectively. The plural Peltier elements 230, 231 are mounted to each of electrodes.

The insulating substrate 211' has a substantially plate-like base 502 having a first plate surface, not visible in FIG. 5, on which the electrodes and Peltier elements 230, 231 are disposed. The insulating substrate 211' has a second, opposite plate surface 211b from which a plurality of fins 134' extend. The fins 134' may suitably be integrally formed with the plate-like base 502 of a thermally conductive, electrically insulating material, such as a ceramic of aluminum oxide or aluminum nitride.

The insulating substrate 212' has a thicker plate-like base 504 through which a plurality of holes or passages 506 extend. Each of the passages 506 extends from a first end 508 of the insulating substrate 212' to a second end 510 of the insulating substrate 212'. The passages 506 extend parallel to each other and are disposed adjacent in a row that extends from side to side of the insulating substrate 212'. The passages 506 form a portion of the supply conduit 132. In an embodiment of the portable thermal pack 102 that includes the thermoelectric module 118', a portion of the conduit 132 is fluid connected between the inlet 122 and the passages 506 at the first end 508, and a portion of the conduit 132 is fluid connected between the fluid outlet 124 and the passages 506 at the second end 510. In this case, the thermal exchange between the thermoelectric module 118' and liquid within the supply conduit 132 occurs in the passages of the insulating substrate 212'.

Referring again to the embodiment of FIGS. 1 and 4, it will be appreciated that in the embodiment having a separate thermally conductive element 130, the thermally conductive element 130 may include interior passages similar to the passages 506 of FIG. 5, such that thermal exchange between the thermally conductive element 130 and the liquid within the supply conduit 132 thus occurs within the passages of the thermally conductive element 130.

Referring to FIG. 2, the printed circuit board 116 in this embodiment supports a control circuit 140, a power storage unit 142, a DC regulator 144, and a double pole, double throw switch 146. It will be appreciated that one or more of the elements discussed above, for example, the power storage unit 142, may be supported within the housing 114 in some way other than being mounted to the printed circuit board 116.

The power storage unit 142 is one or more devices that store power so that the thermal pack 102 may be portably powered. In this embodiment, the power storage unit 142 comprises one or more batteries, by way of example, having a positive terminal 142a and a negative terminal 142b. The double pole double throw switch 146 in this embodiment is operably connected to selectively and alternately connect the first and second terminals 126, 128 of the thermoelectric module 118 to the positive and negative terminals 142a and 142b of the power storage unit 142. In other words, the switch 146, which may suitably be a relay, controllably reverses the polarity of the DC voltage applied to the thermoelectric module 118. In this way, the switch 146 is used to control whether the module 118 provides cooling to the fluid in the supply conduit 132 (see FIG. 1), or heating to the fluid in the supply conduit 132. The control circuit 140 is operably connected to control the operation of the switch 146. It will be appreciated that other methods and devices may be used to control the polarity of the voltage applied to thermoelectric module 118 terminals 126, 128.

The DC regulator 144 is operably connected to control a variable voltage provided to the pump 120 from the power storage unit 142. Such voltage regulators are known. The control circuit 140 is operably connected to control the output voltage of the DC regulator 144 provided to the pump 120. It will be appreciated that the other DC regulator 145 is connected in the path between the power storage unit 142 and the switch 146, so as to provide a variable voltage to the thermoelectric module 118 under the control of the control circuit 140.

The control circuit 140 also includes a wireless communication circuit 150 configured to receive wireless signals including control information. In this embodiment, the information is received from the wireless device 106. However, such control information may be received from other devices. In addition, the control circuit 140 can receive temperature information from any of the temperature sensors 148. For temperature sensors 148 in the garment 112 (see FIG. 1), the temperatures sensors 148 may suitably be wireless RFID devices configured to communicate temperature information using power from signals transmitted by the wireless communication circuit 150. However, one or more of the temperature sensors 148 may be hardwired if necessary.

The received control information can include information identifying a value of at least one operating parameter of the thermoelectric module 118. Accordingly, the control information may include information identifying whether heating or cooling is to be applied, or in other words, the position of the switch 146. The control information may include the level of heating and/or cooling, which could corresponding to the voltage levels of either or both of the DC regulators 144, 145. To this end, the wireless device 106 has a user interface that allows a user to either specify operating levels for the pump 120 and/or the thermoelectric module 118, or run a preprogrammed sequence of parameter sets that operate based on time. For example, the wireless device 106 may include a program that alternates heating and cooling (via appropriate control information that cause the control circuit 140 to operate the switch 146) every fifteen minutes. Such a program can include level adjustments to alter the outputs of the thermoelectric module 118 and pump 120.

Accordingly, the control circuit 140 is a programmable device, processor, microcontroller, or the like, that is configured to generate control signals to the DC regulators 144, 145 and the switch 146. In general, the control circuit 140 provides such control signals based on the content of control information received from the wireless communication circuit 150. However, the control circuit 140 may also include internal programs that adjust certain parameters levels for example based on inputs of sensors 148, other sensors, not shown, but which relate to ambient air temperature, the status of the power storage device 142, etc.

In one embodiment, the control circuit 140 includes logic or programming capable of carrying out a control algorithm to regulate the temperature of the fluid in the conduit 104 (or supply conduit 132 to a set point which is based on a user setting. The control algorithm may be any suitable P, PI or PID control algorithm that generates control signals based on control information as well at temperature information sensed at one or more of the sensors 148. It will be appreciated that the sensors 148 in the garment 112 may be wireless devices such as RFID devices that use incident wireless signals from the wireless communication circuit 150

In operation, and with reference to both FIG. 1 and FIG. 2, the control circuit 140 provides signals to the switch 146 and the voltage regulators 144, 145 to control the operations of the thermoelectric module 118 and the pump 120. The pump 120 pumps fluid through the supply conduit 132 into the application conduit 104 via the fluid outlet 124 and the inlet 108. The fluid in the application conduit 104 exchanges heat with the body part to which the garment 112 is attached. In cooling mode, the fluid receives heat from the body part, which increases the temperature of the fluid in exiting the conduit 104 via the outlet 110. In heating mode, the fluid transfers heat to the body part, which decreases the temperature of the fluid exiting the conduit 104 via the outlet 110.

The return fluid flows out of the outlet 110 and into the supply conduit 132 and exchanges heat with the thermoelectric module 118 via the thermally conductive device 130. In cooling mode, current through the thermoelectric module causes the substrate 212 to be cooler than the substrate 211 and preferably cooler than the incoming fluid. The thermoelectric module 118 thus removes heat from the fluid via the thermally conductive device 130. The Peltier elements 131, 132 cooperate to maintain a temperature gradient from the second insulating substrate 212 to the first insulating substrate 211. In the cooling mode, the Peltier elements 131, 132 cooperate to maintain a higher temperature at the first insulating substrate 211. Accordingly, in the cooling mode, the heat transferred from the fluid in the supply conduit 132 to the second insulating substrate 212 tends to drive the temperature of the first insulating substrate 211 upwards. The heat sink fins 134 operate to increase the exchange of such heat with the cooler ambient air.

In the heating mode, the Peltier elements 131, 132 operate in reverse fashion. In the heating mode, the Peltier elements 131, 132 cooperate to maintain a higher temperature at the second insulating substrate 212 and a lower temperature at the first insulating substrate 211. Accordingly, in the heating mode, the heat transferred to the fluid in the supply conduit 132 from the second insulating substrate 212 tends to drive the temperature of the first insulating substrate 211 downward. The heat sink fins 134 operate to increase the exchange of such heat with the warmer ambient air.

In the cooling mode, the fluid cooled by the thermoelectric module 118 flows back to the fluid outlet 124 and into the inlet 108 of the conduit 104 that exchanges heat with the body part. Similarly, in the heating mode, the fluid heated by the thermoelectric module 118 flows back into the fluid outlet 124 and into the inlet 108 of the conduit 104 that exchanges heat with the body part.

It will thus be appreciated that the system 100 provides a portable device that is capable of selectively and even alternately providing heating and cooling therapy to a body part.

One of the advantages of the embodiments described herein is that the system 100 can leverage ambient temperature to generate heat for the thermal therapy fluid. In particular, in the heat therapy operation, the thermoelectric module 118 generate a heat differential between the cool side of the module 118, insulating substrate 211, and the higher temperature side of the module, insulating substrate 212. To obtain a desired fluid temperature, the control circuit 140 need only create a differential between the ambient air (on insulating substrate 211) and the temperature of substrate 212 required to obtain the desired fluid temperature. Thus, in a warm environment the thermoelectric module 118 would require significantly less energy to heat the fluid.

The above described embodiments are merely exemplary, and those of ordinary skill in the art may readily devise their own modifications and implementations that incorporate the principles of the present invention and fall within the spirit and scope thereof.

What is claimed is:

1. A system for applying thermal therapy, comprising:
a wearable garment configured to be worn on a body of a person to which the thermal therapy is to be applied;
at least one conduit having a segment that is integrated into the wearable garment such that heat exchange occurs between the body of the person and a fluid within the at least one conduit, the at least one conduit having further segments extending away from the wearable garment that have an inlet end and outlet end; and
a wearable fabric pack with at least one clasp for securing the wearable fabric pack to the body of the person, the wearable fabric pack supporting at least one thermoelectric module, a power storage unit, a pump, a fluid inlet configured to be operably coupled to the outlet end of the at least one conduit, and a fluid outlet configured to be operably coupled to the inlet end of the at least one conduit,
wherein the pump is operably connected to pump the fluid from the fluid inlet to the fluid outlet,
wherein the at least one thermoelectric module is coupled to generate a thermal change in the fluid disposed between the fluid inlet and the fluid outlet,
wherein the power storage unit is operably coupled to provide operating power to the pump and the at least one thermoelectric module, and
wherein the at least one thermoelectric module includes:
a first electrically non-conductive substrate having a rectangular block-shaped body with six faces;
a plurality of heat sink fins operably coupled directly to a first face of the body of the first electrically non-conductive substrate to exchange heat between ambient air and the first electrically non-conductive substrate;
a second electrically non-conductive substrate having a rectangular block-shaped body with six faces, the body defining a plurality of passages through which the fluid of the at least one conduit flows to exchange heat between the fluid and the at least one thermoelectric module, the plurality of passages extending parallel to one another, each respective passage of the plurality of passages extending from a respective first opening defined in a first face of the body of the second electrically non-conductive substrate to a respective second opening defined in a second face of the body of the second electrically non-conductive substrate, the second face of the body of the second electrically non-conductive substrate being opposite and parallel to the first face of the body of the second electrically non-conductive substrate; and
a plurality of Peltier elements disposed between a second face of the body of the first electrically non-conductive substrate and a third face of the body of the second electrically non-conductive substrate, the second face of the body of the first electrically non-conductive substrate being opposite and parallel to the first face of the body of the first electrically non-conductive substrate.

2. The system of claim 1, wherein the at least one conduit is incorporated into a pad.

3. The system of claim 1, further comprising a control circuit, the control circuit operably connected to control at least one operating parameter of the at least one thermoelectric module to controllably vary the thermal change in the fluid.

4. The system of claim 3, wherein the control circuit includes a wireless communication circuit configured to receive wireless signals including control information, and wherein the control circuit is further configured to control the at least one operating parameter of the at least one thermoelectric module based on the received control information.

5. The system of claim 4, wherein the control circuit is further configured to controllably remove heat from the fluid, or add heat to the fluid.

6. The system of claim 5, wherein the plurality of Peltier elements are of alternating doping types and are series connected by alternating doping type between first and second electrical terminals.

7. The system of claim 6, further comprising a double pole double throw switch operably connected to the first and second electrical terminals to provide selectively alternate voltage polarity to the at least one thermoelectric module.

8. The system of claim 1, wherein the fluid is water.

9. The system of claim 1, wherein the power storage unit comprises at least one battery.

10. The system of claim 1, wherein the plurality of Peltier elements are of alternating doping types and are series connected by alternating doping type between first and second electrical terminals.

11. The system of claim 1, further comprising a control circuit and at least one temperature sensor, the at least one temperature sensor supported on the wearable garment and communicatively coupled to the control circuit, and wherein the control circuit is configured to control at least one operating parameter of the at least one thermoelectric module based at least in part on temperature information received from the at least one temperature sensor.

12. The system of claim 11, wherein another of the at least one temperature sensor is disposed within the wearable fabric pack.

13. The system of claim 11, wherein the control circuit is configured to control the at least one operating parameter based on a P, PI, or PID control algorithm.

14. The system of claim 11, further comprising a voltage regulator operably connected between the power storage unit and the at least one thermoelectric module, and wherein the control circuit is configured to control the at least one operating parameter of the at least one thermoelectric module by controlling an output voltage of the voltage regulator.

15. The system of claim 1, wherein the wearable fabric pack includes an opening between and interior and exterior thereof, and wherein a fan is mounted in the opening.

* * * * *